United States Patent [19]

Chazov et al.

[11] Patent Number: 4,698,419

[45] Date of Patent: Oct. 6, 1987

[54] HEXAPEPTIDE

[75] Inventors: Evgeny I. Chazov; Vladimir N. Smirnov; Valentin A. Vinogradov; Vladimir M. Polonsky; Valentina A. Tischenko; Mikhail I. Titov; Zhanna D. Bespalova; Boris L. Pekelis, all of Moscow, U.S.S.R.

[73] Assignee: Vsesojuzny Kardiologichesky Nauchny Tsentr Akademii Meditsinskikh Nauk SSSR, Moscow, U.S.S.R.

[21] Appl. No.: 835,114

[22] PCT Filed: Apr. 24, 1985

[86] PCT No.: PCT/SU85/00031

§ 371 Date: Feb. 5, 1986

§ 102(e) Date: Feb. 5, 1986

[87] PCT Pub. No.: WO86/00621

PCT Pub. Date: Jan. 30, 1986

[30] Foreign Application Priority Data

Jul. 16, 1984 [SU] U.S.S.R. .............................. 3772913

[51] Int. Cl.$^4$ .............................................. C07K 7/06
[52] U.S. Cl. ................................................... 530/329
[58] Field of Search ........................................ 530/329

[56] References Cited

U.S. PATENT DOCUMENTS 4,428,941  1/1984  Calibert et al. ...................... 530/329
4,578,217  3/1986  Vnek et al. ........................... 530/329

OTHER PUBLICATIONS

Article: Assessment of Antienzymatic Therapy of Destructive Pancreatitis, Yu A. Nesterenko; Yu P. Atanov.

*Primary Examiner*—Delbert R. Phillips
*Attorney, Agent, or Firm*—Ladas & Parry

[57] ABSTRACT

A novel hexapeptide having the following structure:

Phe-Ala-Gly-Phe-Gly-Arg.

The hexapeptide according to the present invention has a hepatoprotective effect.

1 Claim, 1 Drawing Figure

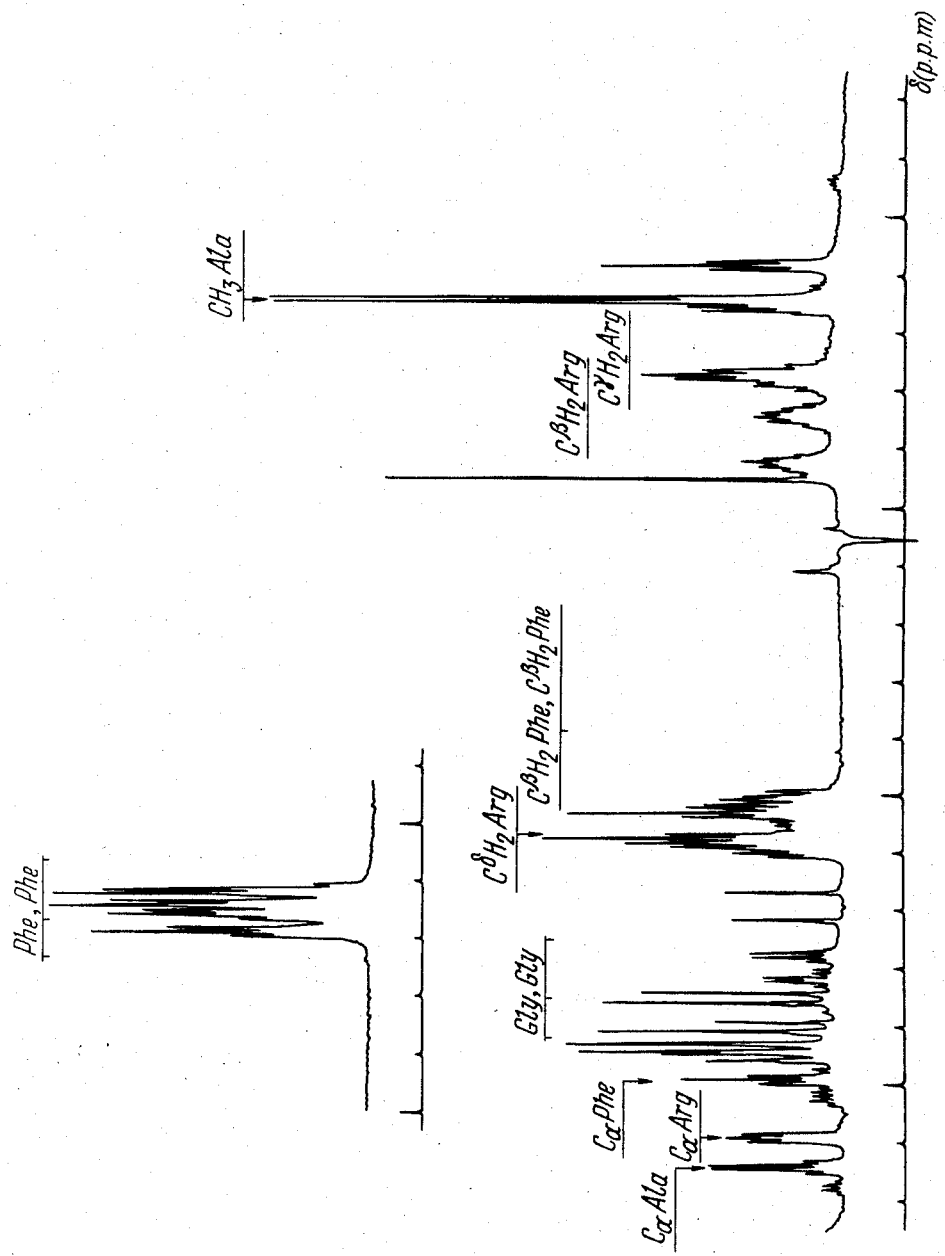

HEXAPEPTIDE

FIELD OF THE INVENTION

The present invention relates to the organic chemistry and, more particularly, to a novel hexapeptide.

BACKGROUND OF THE INVENTION

At the present time for the treatment of acute viral hepatitis, aggravation of chronic hepatitis and hepatocirrhosis synthetic glucocorticoidal hormonal preparations such as prednisolone and the like are most widely administered. These preparations are employed, as a rule, over long periods and cause a great number of complications on the part of various organs and systems. Glucocorticoids bring about atrophy of the cortical layer of adrenal glands, increased arterial pressure, development of steroid diabets, obesity, retention of urine, electrolytical disturbances, osteoporosis phenomena, pahological bone fractures. In the gastro-intestinal tract glucocorticoids frequently cause the formation of ulcers complicated with hemorrhages which provides an especially detrimental effect on the progress of chronic liver diseases. An abrupt cancellation of glucocorticoids results in the development of an acute adrenal insufficiency. Remissions in the treatment with preparations of this class are instable and of short duration. (cf. Scott J., Physiological pharmacological and pathological effects of glucocorticoids on the digestive system, Clin. gastroenterol.m 1981, v. 10, p. 627–652).

Known in the art are hexapeptides of a different structure, for example hexapeptide His-D-Trp-Ala-Trp-D-Phe-Lys-NH$_2$ (Bowers Cy et al., Endocrinology, 1984, v. 114, No. 5, p. 1537–1545) or hexapeptide Tyr-D-Ala-Gly-Phe-Leu-Arg and the like (cf. A. V. Waldman, O. S. Medvedev. Theoretical Prerequisits for Finding New Cardio-Vascular Agents Among Peptides, "Vestnik Akademii Meditsinskikh Nauk SSSR", 1982, No. 5, p. 14–22).

However, the hepatoprotective activity of such compounds is hitherto unknown in the art.

DISCLOSURE OF THE INVENTION

The hexapeptide according to the present invention is novel and hitherto unknown in the literature.

The present invention is directed to the provision of a novel compound-hexapeptide exhibiting a high hepatoprotective activity, causing no side responses and useful in medicine.

This object is accomplished by a novel hexapeptide which, according to the present invention has the following structure: Phe-Ala-Gly-Phe-Gly-Arg The hexapeptide according to the present invention comprises a white powder well soluble in distilled water, physiological solution, ethanol, insoluble in ether, ethylacetate, benzene. Melting point is 154°–156° C., $(\alpha)_D^{25} = +8.4$ (with 0.5 H$_2$O).

BEST MODE FOR CARRYING OUT THE INVENTION

The study of a hepatoprotective effect of the hexapeptide according to the present invention was carried out in comparison with prednisolone on male mice of the line Balb C.

The development of acute hepatitis was induced in mice subjected to a 12-hours' starving by means of D-galactosamine hydrochloride which was administered intraperitoneally diluted in 0.1 ml of a physiological solution in the dose of 700 mg/kg. The control group of animals was administered intraperitoneally with 0.1 ml of a physiological solution. The animals given D-galactosoamine hydrochloride were injected, immediately after its administration, with the hexapeptide according to the present invention (100 μg/kg), prednisolone (5 mg/kg) or a physiological solution (0.1 ml) hypodermally. Repeated injections of the test preparations were made after 6 hours. Each of the groups consisted of 12 animals. The mice were slaughtered by decapitation, blood was collected and in its plasma concentrations of alanine transaminase and glutametedehydrogenase were determined.

The statistical processing of the results obtained was effected using t-criterion. The certain value was regarded as the dirrerence at the level of 95% (at $P<0.05$).

The results thus obtained are shown in Table 1.

TABLE 1

| No. | Groups of animals | Concentration of alanine transaminase, JU/e | Concentration of glutamatedehydrogenase, JU/e |
|---|---|---|---|
| 1. | Control | 113.6 ± 5.5 | 32.5 ± 3.8 |
| 2. | D-galactosamine hydrochloride + physiological solution | 170.8 ± 10.1* | 121.6 ± 16.0* |
| 3. | D-galactosamine hydrochloride + hexapeptide of this invention | 115.4 ± 5.2** | 62.8 ± 4.9** |
| 4. | D-galactosamine hydrochloride + prednisolone | 151.2 ± 14.3 | 104.5 ± 10.1 |

*The difference between Group 1 and Group 2 is certain
**The difference between Group 2 and Group 2 is certain As it follows from the above Table, D-galactosamine hydrochloride causes a substantial increase of concentrations of the studied enzymes in the blood plasma. In this case the concentration of alanine transaminase increased by 1.5 times and that of glutamatedehydrogenase—by more that 3 times. The hexapeptide according to the present invention substantially fully blocked the increase of concentrations of alanine transaminase and reduced by 2 times the concentration of glutamatedehydrogenase. In the case of administration of prednisolone a trend was observed towards reducing the values of the studied parameters.

The hexapeptide according to the present invention was also studied on an experimental model of an acute liver injury in male rats of the V-star line induced by means of carbon tetrachloride. After a 12-hours' starvation the rats were given CCl$_4$ in the concentration of 1 mg/kg diluted in olive oil intraperitoneally. After administration of CCl$_4$ the rats were injected with the hexapeptide according to the present invention in different doses (10, 30, 100 and 300 μg/kg). Repeated injections of the hexapeptide according to the invention were effected after 6, 24, and 30 hours. The control group of animals was given, instead of the hexapeptide of this invention, a physiological solution (0.2 ml). All the test groups of animals consisted of 13 rats. Concentrations of alanine transaminase and glutamatedehydrogenase were determined in the rats blood. The results obtained in these experiments are shown in the following Table 2.

TABLE 2

| No. | Groups of animals | Concentration of alanine transaminase, JU/e | Concentration of glutamate-dehydrogenase, JU/e |
|---|---|---|---|
| 1. | Vivarium control | 64.6 ± 3.3 | 17.2 ± 0.6 |
| 2. | Carbon tetrachloride | 4349.3 ± 2285.1 | 5619.7 ± 1201.7* |
| 3. | CCl₄ + hexapeptide of this invention (10 μg/kg) | 4141.5 ± 1094.8 | 1962.0 ± 494.7 |
| 4. | CCl₄ + hexapeptide of this invention (30 μg/kg) | 3037.8 ± 580.8 | 1487.3 ± 301.5** |
| 5. | CCl₄ + hexapeptide of this invention (100 μg/kg) | 2339.8 ± 333.4 | 874.3 ± 118.3** |
| 6. | CCl₄ + hexapeptide of this invention (300 μg/kg) | 2110.1 ± 374.5 | 603.3 ± 118.0** |

*The difference with Group 1 is certain.
**The difference with Group 2 is certain.

As it follows from Table 2 hereinabove, CCl₄ causes a certain increase of a concentration of glutamatedehydrogenase. The increase of alanine transaminase is not statistically significant due to a small number of observations. The hexapeptide according to the present invention lowers both parameters depending on the dose. Especially pronounced is the reduction of a more specific hepatic enzyme-glutamatedehydrogenase.

The hexapeptide according to the present invention has also blocked lethality of rats in the case of using carbon tetrachloride. The results obtained are shown in Table 3. As it follows from this Table, while carbon tetrachloride causes death of 77% of the animals, administration of the hexapeptide according to the present invention in the doses of 100 and 300 μg/kg no lethal cases are observed.

TABLE 3

| Parameters | Dose of the hexapeptide of the invention (μg/kg) | | | | |
|---|---|---|---|---|---|
| | 0 | 10 | 30 | 100 | 300 |
| Number of rats survived after 48 hours | 3 | 6 | 9 | 13 | 13 |
| Lethal cases (%) | 77 | 54 | 30* | 0* | 0* |

*The difference from Group 0 is certain.

A statistical processing in the case of liver injury caused by carbon tetrachloride in respect of the enzymes was effected using t-criterion, while in respect of lethality—by means of $\chi^2$ criterion.

In all of the experiments with the use of the hexapeptide according to the present invention no changes were observed on the part of the cell composition of the blood and basic hemohynamic characteristics. The acute toxicity of the hexapeptide according to the present invention $LD_{50}$ was equal to 120 mg/kg.

The comparison of the hexapeptide of the present invention with somatostatin shows that the hexapeptide is superior over the latter in its efficiency: lethality of 0% as compared to 20% in the case of somatostatin; maximum effective dose is by 15 times lower (100 μg/kg for the hexapeptide and 1.5 mg/kg for somatostatin).

Therefore, in the employed experimental models of an acute hepatitis the hexapeptide according to the present invention certainly lowered concentrations of glutamatedehydogenase and alanine transanimase in blood, the increase of which is characteristic for a pathological process developing in the liver. This points to the availability of hepatoprotective properties in the hexapeptide according to the present invention. Prednisolone when used in a conventionally employed parenteral dose does not provide any pronounced effect on the concentration of the enzymes.

The hexapeptide according to the present invention, as regards its activity, is superior to prednisolone (employed in a 50-times higher dose) and somatostatin (used in a 15-times greater dose). The hexapeptide according to the present invention, i.e. phenylalanyl-alanyl-glycyl-phenylalanyl-glycylarginine is synthesized by a method of a successive building-up of the aminoacid chain by one amino acid, starting from arginine as a free base and activated esters of protected amino acids by removing the protecting groups by way of a catalytical hydrogenolysis and an acidolytic cleavage.

For a better understanding of the present invention, the following example illustrating preparation of the hexapeptide according to the invention is given hereinbelow.

EXAMPLE 1

1.58 g (9.07 mN) of arginine are suspended in 25 ml of dimethylformamide, the solution is added with 3.30 g (9.98 mM) of p-nitrophenyl ester of carbobenzoxy glycin, the mixture is stirred at room temperature for one day. Dimethylformamide is evaporated, the residue is dissolved in 5 ml of methanol and added with 300 ml of ether. The resulting precipitate is filtered-off, washed in the filter with ether and dried in a vacuum desiccator. There are thus obtained 3.09 g (93%) of carbobenzoxyglycyl-arginine with the melting point of 135°–135.5° C., $[\alpha]_D^{25} = +10.3$ (CI, dimethylformamide).

$R_f^1 = 0.25$ (n-butanol:acetic acid:water 3:1:1) (A)

$R_f^2 = 0.54$ (chloroform:methaol:32% acetic acid 60:45:20)(B)

$R_f^3 = 0.33$ (ethylacetate:pyridine:acetic acid:water 45:20:5:11) (C).

3.09 g (8.46 mM) of carbobenzoxy-glycyl-arginine are dissolved in 35 ml of trifluoroacetic acid; a current of dry hydrogen bromide is passed through the resulting solution for one hour. The solvent is evaporated, the residue is added with 150 ml of ether; the resulting precipitate is filtered-off, dissolved in water and treated with an ion-exchange resin Amberlite IR A-410 (OH⁻ form) to the negative reaction on bromine ions. The resin is filtered-off, washed in the filter with methanol and water; the filtrate is evaporated, the remaining water is removed by azeotropic distillation with isopropanol. The residue is dissolved in 25 ml of dimethylformamide, the solution is added with 3.91 g (9.21 mM) of p-nitrophenyl ester of carbobenzoxy-phenylalanine. The reaction mixture is maintained at room temperature for one day. Dimethylformamide is evaporated, the residue is dissolved in 5 ml of methanol and 300 ml of ether are added thereto. The resulting precipitate is filtered-off, washed with ester on the filter and dried in a vacuum desiccator. 3.75 g (86%) of carbobenzoxy-phenylalanyl-glycyl-arginine are thus obtained; melting point 133°–134° C., $[\alpha]_D^{25} = 17.2$ (cI, dimethylformamide), $R_f^1 = 0.30$ (A), $R_f^2 = 0.66$ (B), $R_f^3 = 0.43$ (C).

Carbobenzoxy-glycyl-phenylalanyl-glycyl-arginine is prepared by the method similar to that described for the preparation of carbobenzoxy-phenylalanyl-glycyl-arginine on the basis of 2.71 g (5.28 mM) of the latter and 1.93 g (5.83 mM) of p-nitrophenyl ester of carbobenzoxy-glycin.

2.46 g (82%) of carbobenzoxy-glycyl-phenylalanyl-glycyl-arginine are obtained; melting point is 142°–144° C., $[\alpha]_D^{25} = -17.3$ (CI, dimethylformamide); $R_f^1 = 0.57$ (B), $R_f^2 = 0.35$ (C), $R_f^3 = 0.45$ (n-butanol:formic acid:water 15:3:1).

On the basis of 2.46 g (4.32 mM) of carbobenzoxy-glycyl-phenylalanyl-glycyl-arginine and 1.64 g (4.75 mM) of p-nitrophenyl ester of carbobenzoxyalanine in a manner similar to that described hereinbefore 2.13 g (77%) of carbobenzoxy-alanyl-glycyl-phenylalanyl-glycyl-arginine are obtained with the melting point of 148°–149° C., $[\alpha]_D^{25} = -20.8$ (cI, dimethylformamide); $R_f^1 = 0.64$ (B), $R_f^2 = 0.38$ (C), $R_f^3 = 0.39$ (n-butanol:pyridine:concentrated ammonia:water 20:12:3:15) (D).

From 0.64 g (0.99 mM) of carbobenzoxy-alanyl-glycyl-phenylalanyl-glycyl-arginine and 0.46 g (1.1 mM) of p-nitrophenyl ester of carbobenzoxyphenylalanine in a manner similar to that described hereinabove 0.63 g (81%) of carbobenzoxy-phenylalanyl-alanyl-glycyl-penylalanyl-glycyl-arginine is obtained; melting point is equal to 150°–153° C., $[\alpha]_D^{22} = -3.5$ (cI, MeOH). $R_f^1 = 0.42$ (A), $R_f^2 = 0.70$ (B), $R_f^3 = 0.39$ (C).

0.63 g (0.80 mM) of carbobenzoxy-phenylalanyl-alanyl-glycyl-phenylalanyl-glycyl-arginine is dissolved in 10 ml of methanol and hydrogenated in the presence of a palladium catalyst. The catalyst is filtered-off, washed on the filter with methanol, evaporated, the residue is reprecipitated with ester (100 ml) from methanol and dried in a vacuum desiccator. The resulting product is passed through a column (600×15) with Sephadex SP C-25 and fractioned in a gradient of a pyridineacetate buffer of 0.05–1.00 M.

0.34 g (65%) of phenylalanyl-alanyl-glycyl-phenylalanyl-glycyl-arginine is obtained; melting point is 154°–156° C.; $[\alpha]_D^{25} = +8.4$ (c 0.5, H$_2$O); $R_f^1 = 0.58$ (B), $R_f^2 = 0.32$ (D), $R_f^3 = 0.44$ (n-butanol:pyridine:acetic acid:water 10.5:5:1:7.5).

The amino acid analysis data:
Phenylalanine 2.13 (2), alanine 1.00 (1), glycine 1.97 (2), arginine 0.93 (I).

Individuality of the synthesized hexapeptide is proven by the NMR spectrum (FIG. 1) and by the method of a highly-effective gas-liquid chromatography. The peptide was eluted in one peack at 39.3% of the gradient on the 12.8-th minute.

(Column 250×4.6 mm, Spherisorb ODS, 5μ; mobile phase A; 0.05M KH$_2$PO$_4$; pH 3.0; B:CH$_3$CN; gradient 20%→50% C for 20 minutes; pressure 1,500 psi; rate 1 mm/min; detection at 214 nm).

INDUSTRIAL APPLICABILITY

The hexapeptide according to the present invention exhibits a hepatoprotective effect and can be useful in medicine for the treatment of acute and chronic liver diseases.

We claim:
1. A hexapeptide of the following structure:

Phe-Ala-Gly-Phe-Gly-Arg.

* * * * *